United States Patent [19]

Zine, Jr.

[11] 4,021,340
[45] May 3, 1977

[54] BLOOD SEPARATING COMPOSITION
[75] Inventor: Anthony R. Zine, Jr., Corning, N.Y.
[73] Assignee: Corning Glass Works, Corning, N.Y.
[22] Filed: Nov. 28, 1975
[21] Appl. No.: 636,127
[52] U.S. Cl. .............................. 210/83; 210/515; 210/DIG. 23
[51] Int. Cl.² ........................................ B01D 21/26
[58] Field of Search ............ 23/230 B, 258.5, 259, 23/292; 128/2 F, 214 R, 218 M, 272, DIG. 5; 210/83, 84, 514–518, DIG. 23, DIG. 24; 233/1 A, 1 R, 26; 252/20, 27, 28, 317

[56] References Cited
UNITED STATES PATENTS

| | | | |
|---|---|---|---|
| 3,210,273 | 10/1965 | Taulli | 252/317 X |
| 3,500,603 | 3/1970 | Strack | 52/395 |
| 3,574,135 | 4/1971 | Sampson et al. | 252/317 |
| 3,663,726 | 5/1972 | Waring | 252/28 |
| 3,780,935 | 12/1973 | Lukacs et al. | 210/DIG. 23 |
| 3,920,549 | 11/1975 | Gigliello et al. | 210/DIG. 23 |
| 3,920,557 | 11/1975 | Ayres | 210/DIG. 23 |
| 3,977,982 | 8/1976 | Hertl | 210/DIG. 23 |

OTHER PUBLICATIONS

Kirk–Othmer: Encyclopedia of Chemical Technology.
Chem. Abstracts, 68:116233m (1968).
Billmeyer: Textbook of Polymer Science, p. 506, 1971.
Condensed Chemical Dictionary, 1971.
Chem. Abstracts, 83:181307n, 1975.

*Primary Examiner*—Frank A. Spear, Jr.
*Assistant Examiner*—R. G. Mukai
*Attorney, Agent, or Firm*—James A. Giblin; Clinton S. Janes, Jr.; Clarence R. Patty, Jr.

[57] ABSTRACT

Gel-like compositions useful for separating and partitioning whole blood into serum and clot portions. The composition comprises a polybutene liquid polymer having an inert high surface area inorganic filler dispersed therein, the filler being present in an amount sufficient to impart to the composition a specific gravity ranging from about 1.030 to about 1.090 and a viscosity ranging from about 200,000 to about 850,000 centistokes. When centrifuged in the presence of whole blood, the composition forms a chemical and physical barrier between the serum and clot portions.

9 Claims, No Drawings

BLOOD SEPARATING COMPOSITION

RELATED APPLICATION

U.S. patent application Ser. No. 631,871, filed Nov. 14, 1975 in the name of A. R. Zine entitled "Blood Separating Composition", now abandoned, and assigned to the present assignee.

BACKGROUND OF THE INVENTION

1. Field

This invention is concerned generally with blood collection test tubes or devices which are ultimately used to separate whole blood into serum and clot portions to facilitate analysis of the blood. Specifically, the invention is concerned with an improved gel-like composition which can be used in such blood collection tubes. The composition has physical and chemical properties which, in the presence of whole blood, permit the composition to be centrifuged to a position intermediate that of the serum and clot portions and, hence, form a barrier between the two portions.

2. Prior Art

The specific gravity of whole human blood is generally within the range of about 1.048 to 1.066. It has long been known that such blood can be readily centrifuged to effect a separation of the blood into two major components— a lighter serum portion having a specific gravity within the range of about 1.026 to 1.031 and a heavier clot portion, consisting mainly of red blood cells, having a specific gravity within the range of about 1.092 to 1.095. Such separations of whole blood into its two major components have greatly facilitated physical and chemical analyses of blood and, hence, assisted in the diagnosis and prognosis of many human ailments.

With the advent of modern sophisticated techniques for the analysis of various physical and chemical subcomponents of blood, there has been a general recognition that simple centrifugation of whole blood into its two major components does not necessarily effect an ideal separation for analytical purposes. For example, even though simple centrifugation yields a gross separation of whole blood into serum and clot portions, there still exists an interface between the separated portions which, especially with time, results in the diffusion of various sub-components of one separated portion into the other. Such diffusion can affect the accuracy of various analyses.

In recent years, efforts have been made to overcome the problems associated with simple centrifugation. For example, it is now well known that various materials or devices having a specific gravity between those of the serum and clot portions can be used to assist in the separation and partitioning of the serum and clot portions. One such material consists of a gel-like, relatively inert, viscous composition having a specific gravity within the range of about 1.030 to about 1.050. Typical components of such a composition are a silicone fluid and a particulate silica filler. When whole blood, contained, for example, in a test tube, is centrifuged in the presence of such a composition, the composition, because of its specific gravity and other properties, tends to migrate to a position intermediate the serum and clot portions. Because of its thixotropic nature, the composition ultimately assumes a configuration which discourages and prevents formation of a serum-clot interface, thereby forming a physical and chemical barrier between the serum and clot portions.

Various examples of such silica-silicone fluid compositions are well known in the art and described in detail, for example, in U.S. Pat. No. 3,780,935 to Lukacs and Jacoby and U.S. Pat. No. 3,852,194 to A. R. Zine, both of which are incorporated herein by reference thereto. In the above cited patents, preferred compositions consist essentially of two components—a silicone fluid such as a dimethylpolysiloxane and very fine silica particles which act as a filler to assist in forming a gel-like material having an appropriate specific gravity. Such components have tended to be preferred because they are essentially inert and, in combination, permit control of both specific gravity and viscosity. An improved and stabilized silicone oil-silica composition is disclosed in detail in my related application Ser. No. 532,946, filed Dec. 16, 1974, entitled "Stabilized Blood Separating Composition", and assigned to the present assignee.

Although various silicone oil-silica gel-like materials have been used commercially for blood separating purposes, it can be appreciated that, because of the need for an essentially inert and relatively pure silicone oil, the cost of such gel-like materials is relatively high. Attempts have been made recently to find or develop other, preferably less expensive, fluids having essentially the same desirable properties as the silicone fluids. See, for example, my recently filed patent application cited above as a related application and which discloses the use of mineral oil as a less expensive fluid.

Quite surprisingly, I have found that there exists another relatively simple and inexpensive class of materials which is ideally suitable as one component of blood separation barriers. This discovery is rather surprising since, prior to my discovery disclosed in detail below, the materials had not been used associated with the separation of blood components although the use of hydrocarbons in general has been suggested in my earlier patent, U.S. Pat. No. 3,852,194.

SUMMARY OF THE INVENTION

The composition useful for separating whole blood into serum and clot portions is a thixotropic, two component system comprising, in combination, a polybutene liquid polymer having dispersed therein an essentially inert inorganic filler in a quantity sufficient to impart to the total composition a specific gravity ranging from about 1.030 to 1.090 and a viscosity ranging from about 200,000 to 850,000 centistokes. In a very preferred embodiment, the composition comprises a polybutene having dispersed therein a particulate siliceous filler having a surface area of at least about 50 $m^2/g$. A very preferred composition has a specific gravity ranging from about 1.037 to 1.050 and a thixotropic index ranging from about 2 to 6. The composition is used to separate and partition whole blood into serum and clot portions by placing both the composition and whole blood into a container adapted to be centrifuged, and centrifugating the mixture until the composition assumes a position intermediate the serum and clot portions of the blood. In a very preferred embodiment, the composition is initially contained in an evacuated test tube into which blood can be drawn, thus providing a closed blood collecting and separating system.

SPECIFIC EMBODIMENTS

To those skilled in the art of grease formulation, it is well known that the addition of various solid fillers can be used to control the viscosity and thixotropy of various organic liquids, particularly the alkanes, alkenes, polyalkenes, and polyisoalkenes, which are widely used for lubricating and other purposes. I am unaware, however, of the use of polybutene liquid-filler gel-like materials for blood separation purposes.

The liquid polymer base for my composition comprises a liquid polybutene having dispersed therein an inert filler. Various polybutene liquid polymers which can be used according to this disclosure are described in a brochure entitled "Amoco Polybutenes" Bulletin 12-H, published by Amoco Chemicals Corp., Chicago, Illinois. The expression polybutene liquid polymer, or its equivalent, refers to the viscous, non-drying polymers of butene and/or isobutene having an average molecular weight such that the polymer is in liquid form; preferably having a molecular weight ranging from about 320 to 2300. The inert filler which is added to the polybutene to control specific gravity, viscosity, and thixotropy, is an essentially inert, particulate inorganic material having a relatively high surface area (>50 $m^2/g$). For example, it is known by those skilled in the art that fillers such as bentonite, silica, talc, and alumina can be added to various oils. In a very preferred embodiment, particulate silica is used in the gel-like compositions described below. Enough filler is added to the polybutene liquid to assure a specific gravity within the range of 1.030 to 1.090, preferably 1.037 to 1.050 and a thixotropic index ranging from about 2 to 6. Thixotropic indices were measured using a Brookfield Viscometer and herein refer to the ratio of viscosity at 1 rpm to the viscosity at 10 rpm.

In one preferred embodiment, the gel-like compositions of this disclosure are placed into individual test tubes of the type disclosed in U.S. Pat. No. 3,852,194 and the tubes are then evacuated to a residual pressure of about 1/10th of an atmosphere. The amount of gel-like material in each tube (16 × 100 mm) is about 1 to 4 grams, preferably about 2 grams. Each tube is capable of drawing in about 10 ml. of whole blood. In use, the tube is used to draw whole blood via a needle in the rubber stopper and the tube and its contents are then centrifuged until the gel-like material migrates to a position intermediate the clot and serum portions and forms a physical and chemical seal between the two portions. As a practical matter, the separation is complete after about 10 minutes of centrifugation at 1100 RCF. After separation, the stopper is removed and the serum portion can be readily removed or poured off without disturbing the intermediate gel-like material which acts as a partitioning seal.

In the examples below, three different polybutene liquid polymers were used with the described fillers to prepare three blood separating compositions. The polymers were obtained commercially from Amoco Chemicals Corp. under product designation H-25, H-35, and H-100. These products correspond to Sample Nos. 1, 2, and 3, respectively and had the following properties as described in the cited Bulletin 12-H, except for viscosity, which was measured at room temperature using a Brookfield Viscometer, No. 6 spindle.

Table I

| (Polybutenes) | Sample No. | | |
|---|---|---|---|
| | 1 | 2 | 3 |
| Average Molecular Weight | 610 | 660 | 920 |
| Viscosity (cs - room temperature) | 3,000 | 6,000 | 26,000 |
| Specific Gravity (60/60° F.) | 0.8633 | 0.8729 | 0.8816 |

The particulate fillers used below consisted of finely divided silica particles having a surface area of about 120 $m^2/g$. Such filler was obtained from Philadelphia Quartz Co. under the product designation QUSO WR-82.

In the examples below, samples of whole blood were successfully separated into serum and clot portions by centrifuging the blood samples at 1100 RCF for 10 minutes in the presence of about 2 g of the indicated polybutene-silica compositions previously placed in a 16 × 100 test tube which was stoppered and evacuated to a residual pressure of 1/10th atmosphere.

EXAMPLES

Whole blood samples (about 10 ml. each) were successfully separated into serum and clot portions using gel-like compositions prepared by mixing the indicated ingredients to form polybutene-filler compositions having the respectively indicated properties of specific gravity, viscosity, and thixotropic index.

Table II

| Composition No. | Compositions Constituent | Parts by Weight |
|---|---|---|
| 1 | Polybutene (Sample No. 1) | 100 |
| | Silica Filler | 41 |
| 2 | Polybutene (Sample No. 2) | 100 |
| | Silica Filler | 38 |
| 3 | Polybutene (Sample No. 3) | 100 |
| | Silica Filler | 34 |

The above compositions had the following properties:

Table III

| Composition No. | Specific Gravity | Viscosity (CS) | Thixotropic Index |
|---|---|---|---|
| 1 | 1.040 | 750,000 | About 4 |
| 2 | 1.040 | 580,000 | 3.2 |
| 3 | 1.040 | 850,000 | About 4 |

COMPARATIVE EXAMPLES

To determine the effect, if any, of the polybutene-silica composition on common blood chemistries, the gel-like material of composition No. 1 was compared with a silicone fluid-silica gel-like material of the type described in patent application Ser. No. 532,946 cited above. The comparative gel-like composition had the following composition:

Table IV

| Components | Parts by Weight |
|---|---|
| Silicone Fluid (dimethylpolysiloxane) | 100 |
| Silica Filler (about 100 $m^2/g$) | 15 |
| Stabilizer (DC-190) | 0.0173 |

Using identical evacuated test tubes containing the Example 1 composition of Ser. No. 532,946 and the composition No. 1 of this disclosure, blood samples from donors were analyzed at a local hospital using an SMA 12/60 Blood Analyzer, Technicon Instruments, Inc. Below is a summary of 15 pairs of results.

Table V

| Blood Constituent | | Comparison Using Composition No. 1 (polybutene) | Using Comparative Composition (silicone oil) |
|---|---|---|---|
| CA | (mg %) | 9.80 | 9.85 |
| IPHOS | (mg %) | 3.65 | 3.65 |
| GLU | (mg %) | 100.5 | 100.7 |
| BUN | (mg %) | 17.9 | 17.9 |
| URAC | (mg %) | 5.34 | 5.33 |
| CHOL | (mg %) | 215.6 | 218.7 |
| TP | (gm %) | 7.15 | 7.19 |
| ALB | (gm %) | 4.65 | 4.61 |
| TBIL | (mg %) | .50 | .49 |
| APHOS | (mU/ml) | 50.9 | 51.1 |
| LDH | (mU/ml) | 179.9 | 185.3 |
| SGOT | (mU/ml) | 33.9 | 34.7 |

The above results can be deemed clinically identical, thus indicating that the use of the polybutene fluids have no known adverse effect on at least the twelve known and common blood constituents indicated.

Given this disclosure, it is thought that numerous variations will occur to one skilled in the art. Accordingly, it is intended that the above examples should be considered illustrative only and that the scope of this invention should be limited only by the appended claims.

I claim:

1. A method of separating a sample of whole blood into serum and clot portions comprising the steps of:
   1. placing into a container adapted to be centrifuged a quantity of whole blood and a quantity of thixotropic, water-insoluble composition comprising a polybutene liquid polymer having an inert inorganic filler dispersed therein in a quantity sufficient to provide a specific gravity in the composition of 1.030 to about 1.090, a thixotropic index ranging from about 2 to 6, and a viscosity ranging from about 200,000 to 850,000 centistokes; and
   2. centrifuging the container under conditions sufficient to cause the blood to separate into serum and clot portions with the composition migrating to a position intermediate the serum and clot portions.

2. The method of claim 1 wherein the specific gravity of the composition ranges from 1.037 to 1.050.

3. The method of claim 1 wherein the inert filler comprises finely divided silica particles having a surface area of at least 50 $m^2/g$.

4. The method of claim 1 wherein the composition comprises about 34 to 41 parts by weight silica particles, about 100 parts by weight polybutene liquid having a molecular weight ranging from about 610 to 920, and has a specific gravity ranging from about 1.037 to 1.050.

5. The method of claim 1 wherein the composition is contained in an individual test tube, the tube being stoppered and capable of receiving about 10 ml. of whole blood.

6. The method of claim 5 wherein the test tube has a volume of about 15 ml. and the amount of composition contained therein is about 1 to 4 grams.

7. A thixotropic composition useful for separating whole blood into serum and clot portions and comprising a polybutene liquid polymer having dispersed therein an essentially inert inorganic filler in a quantity sufficient to impart to the total composition a specific gravity ranging from about 1.030 to 1.090, a thixotropic index ranging from about 2 to 6, and a viscosity ranging from about 200,000 to 850,000 centistokes.

8. The composition of claim 7 wherein the inert filler comprises finely divided silica particles having a surface area of at least 50 $m^2/g$.

9. The composition of claim 7 wherein the specific gravity ranges from about 1.037 to 1.050.

* * * * *